US012672906B2

(12) United States Patent
Hearn et al.

(10) Patent No.: US 12,672,906 B2
(45) Date of Patent: Jul. 7, 2026

(54) SURGICAL ASSEMBLY, SYSTEM AND ELECTRODE ASSEMBLY

(71) Applicant: ALESI SURGICAL LIMITED, Cardiff (GB)

(72) Inventors: George Hearn, Cardiff (GB); Dominic Griffiths, Cowbridge (GB); Francis Kweku Egyin Amoah, Cardiff (GB); Jason Brewer, Cardiff (GB)

(73) Assignee: ALESI SURGICAL LIMITED, Cardiff (GB)

( * ) Notice: Subject to any disclaimer, the term of this patent is extended or adjusted under 35 U.S.C. 154(b) by 233 days.

(21) Appl. No.: 16/624,733

(22) PCT Filed: Jun. 20, 2018

(86) PCT No.: PCT/GB2018/051725
§ 371 (c)(1),
(2) Date: Dec. 19, 2019

(87) PCT Pub. No.: WO2018/234803
PCT Pub. Date: Dec. 27, 2018

(65) Prior Publication Data
US 2021/0153926 A1      May 27, 2021

(30) Foreign Application Priority Data
Jun. 20, 2017      (GB) ..................................... 1709835

(51) Int. Cl.
*A61B 18/12*          (2006.01)
*A61B 17/32*          (2006.01)
(Continued)

(52) U.S. Cl.
CPC .. *A61B 18/1206* (2013.01); *A61B 17/320068* (2013.01); *A61B 18/14* (2013.01);
(Continued)

(58) Field of Classification Search
CPC ........ A61B 18/1206; A61B 17/320068; A61B 18/14; A61B 2018/00077;
(Continued)

(56) References Cited

U.S. PATENT DOCUMENTS 4,191,189 A * 3/1980 Barkan .................. G10K 15/06
                                                  606/128
5,160,334 A    11/1992 Billings et al.
(Continued)

FOREIGN PATENT DOCUMENTS

GB          2531412 A      4/2016
JP     2001346804 A      12/2001
(Continued)

OTHER PUBLICATIONS

UK Intellectual Property Office, Search Report, GB1709835.1, Feb. 9, 2018, 5 pages.
(Continued)

*Primary Examiner* — Daniel W Fowler
*Assistant Examiner* — Lindsay Regan Lancaster
(74) *Attorney, Agent, or Firm* — Quarles & Brady LLP

(57)                ABSTRACT

A surgical assembly and system are disclosed for use in performing a surgical procedure on a patient. The assembly comprises a surgical tool, the tool being arranged to receive a first signal for use in cutting or cauterizing tissue of the patient during the surgical procedure and an electrode disposed upon the tool. The assembly further comprises an electrical generator communicatively couplable with the electrode, for generating a second signal for use in generating an electrical field from the electrode proximate a site of the surgical procedure, for removing particles suspended proximate the surgical site. The assembly further comprises a controller for controlling the application of the second signal to the electrode, a sensing arrangement for sensing an
(Continued)

400 ⤴ activation status of the first signal, the sensing arrangement being communicatively coupled with the controller and arranged to output a sensing signal to the controller in dependence of the activation status of the first signal. The controller is arranged to enable the application of the second signal to the electrode upon receiving a sensing signal representative of an activation of the first signal. An electrode assembly comprising a plurality of electrically conductive elements for use with a surgical tool is also disclosed.

13 Claims, 10 Drawing Sheets

(51) Int. Cl.
| | | |
|---|---|---|
| *A61B 18/14* | (2006.01) | |
| *A61B 18/00* | (2006.01) | |

(52) U.S. Cl.
CPC .............. *A61B 2018/00077* (2013.01); *A61B 2018/00083* (2013.01); *A61B 2018/00595* (2013.01); *A61B 2018/00601* (2013.01); *A61B 2018/00654* (2013.01)

(58) Field of Classification Search
CPC ........... A61B 2018/00083; A61B 2018/00595; A61B 2018/00601; A61B 2018/00654; A61B 18/08; A61B 2018/00827; A61B 2018/1266; A61B 2090/061; A61B 2218/008; A61B 18/00; A61B 2018/00577; A61B 2018/00625; A61B 2018/00708; B03C 3/41; B03C 3/68
See application file for complete search history.

(56) References Cited

U.S. PATENT DOCUMENTS

| | | | |
|---|---|---|---|
| 8,795,276 | B2 | 8/2014 | Dietz et al. |
| 11,357,564 | B2 * | 6/2022 | Shvetsov ........... A61B 18/1402 |

| | | | | |
|---|---|---|---|---|
| 2008/0234674 | A1 * | 9/2008 | McClurken .......... | A61B 18/148 |
| | | | | 606/49 |
| 2012/0067212 | A1 * | 3/2012 | Warren .................. | A61B 18/00 |
| | | | | 95/57 |
| 2012/0286179 | A1 * | 11/2012 | Palmerton .......... | G05B 19/0423 |
| | | | | 340/12.5 |
| 2012/0303016 | A1 | 11/2012 | Fischer et al. | |
| 2013/0197609 | A1 * | 8/2013 | Moore ................. | A61N 1/3756 |
| | | | | 29/25.35 |
| 2014/0228836 | A1 * | 8/2014 | Amoah .................... | B03C 3/40 |
| | | | | 606/34 |
| 2014/0303615 | A1 * | 10/2014 | Amoah .............. | A61B 18/1233 |
| | | | | 606/34 |
| 2015/0088117 | A1 * | 3/2015 | Gilbert ............... | A61B 18/1206 |
| | | | | 606/34 |
| 2015/0182708 | A1 | 7/2015 | Barnard | |
| 2015/0282873 | A1 | 10/2015 | Batchelor et al. | |
| 2016/0166310 | A1 * | 6/2016 | Stewart .............. | A61B 18/1492 |
| | | | | 606/34 |
| 2016/0338766 | A1 | 11/2016 | Ginnebaugh et al. | |
| 2017/0014175 | A1 * | 1/2017 | Takashino .......... | A61B 18/1445 |
| 2017/0086915 | A1 | 3/2017 | Batchelor et al. | |
| 2017/0231682 | A1 * | 8/2017 | Avcioglu ............. | H03K 17/962 |
| | | | | 606/13 |
| 2017/0333119 | A1 * | 11/2017 | Truckai ................ | A61B 18/149 |

FOREIGN PATENT DOCUMENTS

| | | |
|---|---|---|
| WO | 2006017754 A1 | 2/2006 |
| WO | 2007005159 A1 | 1/2007 |
| WO | 2009105488 A2 | 8/2009 |
| WO | 2011010148 A2 | 1/2011 |
| WO | 2016024130 A1 | 2/2016 |
| WO | 2017053945 A1 | 3/2017 |

OTHER PUBLICATIONS

UK Intellectual Property Office, Search Report, GB1810165.9, Nov. 30, 2018, 5 pages.
PCT International Search Report and Written Opinion, PCT/GB2018/051725, Nov. 23, 2018, 14 pages.

* cited by examiner (d)

(e)

(f)

Voltage setpoint

Current signal

Gain trimmed to
match output
resistance

+

Compensated
voltage setpoint

300

301

(a)

(b)

SURGICAL ASSEMBLY, SYSTEM AND ELECTRODE ASSEMBLY

CROSS-REFERENCE TO RELATED APPLICATIONS

This application represents the national stage entry of PCT International Application No. PCT/GB2018/051725 filed on Jun. 20, 2018 and claims priority to Great Britain Patent Application 1709835.1 filed on Jun. 20, 2017. The contents of these applications are hereby incorporated by reference as if set forth in their entirety herein.

The present invention relates to a surgical assembly, a surgical system and an electrode assembly.

Particulate matter in aerosol form is commonly encountered during surgical procedures. For example, it can be either utilized to deliver a therapeutic agent or can be experienced as a result of performing a surgical procedure. Examples of particulate-based therapeutic agents are the delivery of agents for effecting rapid clotting of blood or for treating diseases such as cancer. A common example of particulate matter created as a result of performing a surgical procedure is that experienced when using "energy-based" surgical instruments. Energy-based surgical instruments are powered in some manner in order to deliver a therapeutic effect such as cutting or coagulating tissue. Although there are several modes of action such as radiofrequency (RF), ultrasonic and laser, all of these energy-based instruments create particulate matter as a by-product of their mode of action.

Particulate matter created in an aerosol form by energy-based instruments is problematic for at least two reasons. Firstly, it rapidly obscures the visual field of the surgeon, and therefore slows the surgical procedure and creates risk of accidental harm to the patient caused by poor visibility. Secondly there are concerns that long-term exposure to particulate matter created by these instruments may represent a hazard for healthcare workers. Historically vacuum-based systems have been used to extract the aerosol particulate matter from the surgical field. However, because this is a dilution-based process it is inefficient at rapidly removing the particulate matter and improving the visual field quality. In addition to this, and in the case of surgical procedures that require gas insufflation to create an operative space, such as laparoscopic surgery for example, the resulting exchange of gas dries and desiccates tissue which has a detrimental effect for the patient. As a result of this and the fact that vacuum-based systems are loud and cumbersome, the adoption of vacuum-based systems has been poor.

WO2011/010148 discloses an alternative approach for managing particulate matter in surgical procedures via an apparatus for the reduction and removal of surgical smoke and other aerosol particulates generated during electrosurgical procedures. The apparatus generates a stream of electrons from a pointed electrode placed near the surgical site, such as within an abdominal cavity, and the electrons emitted from the electrode attach themselves to the aerosol particles suspended nearby. The apparatus further establishes an electrical potential difference between the electrode and the patient for attracting the ionized particles away from the surgical site and thus improving the surgeon's view of the site.

However, the electrode that is deployed into the abdomen for example, requires an additional incision within the abdominal wall which is undesirable. The effectiveness of the apparatus is also dependent on the positioning of the electrode relative to the site of surgery and other surgical instruments, and is thus subject to the surgeons experience and skill.

We have now devised a surgical assembly, surgical system and an electrode assembly which address at least some of the above-mentioned limitations.

According to a first aspect of the present invention there is provided a surgical assembly for use in performing a surgical procedure on a patient, the assembly comprising:

a surgical tool, the tool being arranged to receive a first signal for use in cutting or cauterizing tissue of the patient during the surgical procedure;

an electrode disposed upon the tool;

an electrical generator communicatively couplable with the electrode, for generating a second signal for use in generating an electrical field from the electrode proximate a site of the surgical procedure, for removing particles suspended proximate the surgical site;

a controller for controlling the application of the second signal to the electrode, the assembly further comprising a sensing arrangement for sensing an activation status of the first signal, the sensing arrangement being communicatively coupled with the controller and arranged to output a sensing signal to the controller in dependence of the activation status of the first signal, wherein the controller is arranged to enable the application of the second signal from the electrical generator to the electrode upon receiving a sensing signal representative of an activation of the first signal.

In an embodiment, the controller is arranged to disable the application of the second signal to the electrode upon receiving a sensing signal representative of a deactivation of the first signal.

In an embodiment, the controller comprises a timing arrangement for disabling the application of the second signal to the electrode a predefined time after receiving a sensing signal representative of a deactivation of the first signal.

In an embodiment, the sensing arrangement comprises a sensor for sensing an activation of one or more actuators that activate(s) the first signal. For example, the actuators may be associated with a surgical generator, such as an electrosurgical generator or an ultrasonic generator, for generating the first signal, and may be disposed upon the tool. Alternatively, or in addition thereto, the sensing arrangement comprises a sensor for directly sensing the first signal.

In an embodiment, the assembly further comprises a surgical generator for generating the first signal and the first signal is communicated to the tool via a cable. Accordingly, the sensor of the sensing arrangement may be arranged to sense the generation or activation of the first signal along the cable.

In an embodiment, the assembly further comprises an override actuator for enabling the application of the second signal to the electrode independently of the activation status of the first signal. It is envisaged that this facility will provide a surgeon with the option of manually activating the second signal for removing particles suspended proximate the surgical site. The override actuator may be disposed on the tool or the electrical generator, and may comprise a push-button, for example, to enable the surgeon to commence a smoke clearing period.

The electrode is disposed upon the tool, and in an embodiment, the electrode extends around the tool, proximate a distal end thereof. The electrode comprises a collar or ring of electrically conductive material disposed upon an electrically insulative carrier. The carrier and collar are centered upon a longitudinal axis of the tool and in an embodiment, the carrier comprises a continuous, peripherally extending window for electrically exposing at least a continuous, circumferentially extending portion of the collar.

In an alternative embodiment, the carrier comprises a plurality of circumferentially separated windows for electrically exposing portions of the collar around the tool. In an embodiment, the windows are shaped, such as square and/or triangular, for electrically exposing a shaped portion of the collar. Alternatively, the collar may be shaped to provide the desired shaping of portions of the collar.

In an embodiment, the tool comprises a handle and a shaft which is coupled at a proximal end thereof to the handle, and wherein the electrode is disposed proximate a distal end of the shaft. The electrode may extend around the tool and particularly the shaft. In an embodiment, the electrode is offset from the shaft and may comprise a linear section of wire, or a rod having a sharpened end. In a further alternative, the electrode may comprise a blade.

In an embodiment, the electrode diverges from the shaft, in a direction which is along the shaft toward a distal end thereof.

In an alternative embodiment, the electrode is disposed upon the tool and comprises a plurality of electrically conductive elements circumferentially separated around the tool. The elements are electrically coupled with a respective electrically conductive pathway which extends to a proximate end of the tool, for communicating the second signal from the electrical generator to the respective element. The elements may comprise electrical wires.

In an embodiment, the tool comprises a handle and a shaft which is coupled at a proximal end thereof to the handle, and the electrode is disposed proximate a distal end of the shaft. In an embodiment, the assembly further comprises a heater for heating a region of the shaft disposed longitudinally between the electrode and the distal end of the shaft.

In an embodiment, the shaft comprises a profiled outer surface at least in the region disposed longitudinally between the electrode and the distal end of the shaft.

In an embodiment, the assembly further comprises a monitoring circuit for monitoring a build-up of material on the shaft in the region disposed longitudinally between the electrode and the distal end of the shaft. The monitoring circuit is further arranged to monitor the total current flowing through the patient due to the current flowing from the electrode to the patient. In a first embodiment, the monitoring circuit comprises a switch which is reconfigurable between a first configuration for coupling the electrode with the tool along a first electrical pathway, and a second configuration for coupling the tool-piece with the surgical generator along a second electrical pathway. The monitoring circuit further comprises a current sensor, such as an ammeter, for monitoring the current flowing directly between the electrode and patient within the first electrical pathway, when the switch is configured in the first configuration, and for separately monitoring the current flowing directly between the electrode and the tool along the second electrical pathway, when the switch is configured in the second configuration.

In alternative embodiment, the monitoring circuit comprises a guard collar disposed around a distal end of the shaft of the tool, and the monitoring circuit comprises a first electrical pathway between the electrode and the guard collar, the first pathway comprising a first current sensor for monitoring the electrical current flowing in the first pathway, namely between the electrode and guard collar. The monitoring circuit further comprises a second electrical pathway between the electrode and patient, the second pathway comprising a second current sensor for monitoring the electrical current flowing in the second pathway, namely between the electrode and the patient.

In an embodiment, the electrode further comprises an electrically conductive pathway which extends from the collar to a proximate end of the tool, for communicating the second signal from the electrical generator to the collar.

In an embodiment, the surgical assembly further comprises at least one relay for switching the application of the first and second signals to the tool, and at least one resistor for enabling the discharge or dissipation of residual charge.

In an embodiment, the tool comprises a tool-piece disposed at a distal end thereof, for performing the surgical procedure. The assembly may further comprise a voltage compensation circuit for maintaining a substantially constant voltage difference between the tool-piece and patient tissue independently of a separation between the tool-piece and the patient tissue. The voltage compensation circuit is arranged to maintain the substantially constant voltage difference as the current passing between the tool-piece and patient tissues varies between $0$-$100\ \mu A$. In an embodiment, the voltage compensation circuit is arranged to set the voltage difference between 3 kV and 15 kV, and preferably between 3 kV and 8 kV.

According to a second aspect of the present invention, there is provided a surgical system for use in performing a surgical procedure on a patient, the system comprising:

a surgical tool, a surgical generator communicatively couplable with the surgical tool, for generating a first signal for use in cutting or cauterizing tissue of the patient during the surgical procedure;

an electrode disposed upon the tool;

an electrical generator communicatively couplable with the electrode, for generating a second signal for use in generating an electrical field from the electrode proximate a site of the surgical procedure, for removing particles suspended proximate the surgical site;

a controller for controlling the application of the second signal to the electrode, the assembly further comprising a sensing arrangement for sensing an activation status of the first signal, the sensing arrangement being communicatively coupled with the controller and arranged to output a sensing signal to the controller in dependence of the activation status of the first signal, wherein the controller is arranged to enable the application of the second signal to the electrode upon receiving a sensing signal representative of an activation of the first signal.

Further features of the surgical system may comprise one or more of the features of the surgical assembly.

According to a third aspect of the present invention, there is provided an electrode assembly for removing particles suspended proximate a site of a surgical procedure performed on a patient, the assembly comprising an electrode comprising a plurality of electrically conductive elements, communicatively couplable with an electrical generator and configured to receive an electrical signal, the assembly further comprising a controller communicatively coupled with a sensing arrangement and which is arranged to receive a sensing signal from the sensing arrangement representative of a proximity of the electrically conductive elements to patient tissue, the controller being arranged to selectively admit the electrical signal to the conductive elements in dependence of the sensing signal.

In an embodiment, the electrode is disposed upon a surgical tool. The sensing arrangement may comprise a plurality of current sensors for separately sensing an electrical current flowing along each conductive element. In the event that the sensed electrical current exceeds a predetermined threshold, which may be indicative of the element passing to close to patient tissue, or otherwise contacting tissue, the sensing arrangement is arranged to output a sensing signal to the controller causing the controller to inhibit or otherwise electrically isolate the conductive element from the electrical generator.

In an embodiment, the controller comprises a switching arrangement for selectively electrically isolating the conductive elements.

In an embodiment, the controller comprises a timer for admitting the electrical signal to the conductive elements according to a timing sequence. The timing arrangement thus enables the elements to be separately addressed by the electrical signal according to a desired sequence.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention may be performed in various ways, and, by way of example only, embodiments thereof will now be described, reference being made to the accompanying drawings in which.

Figure 1:
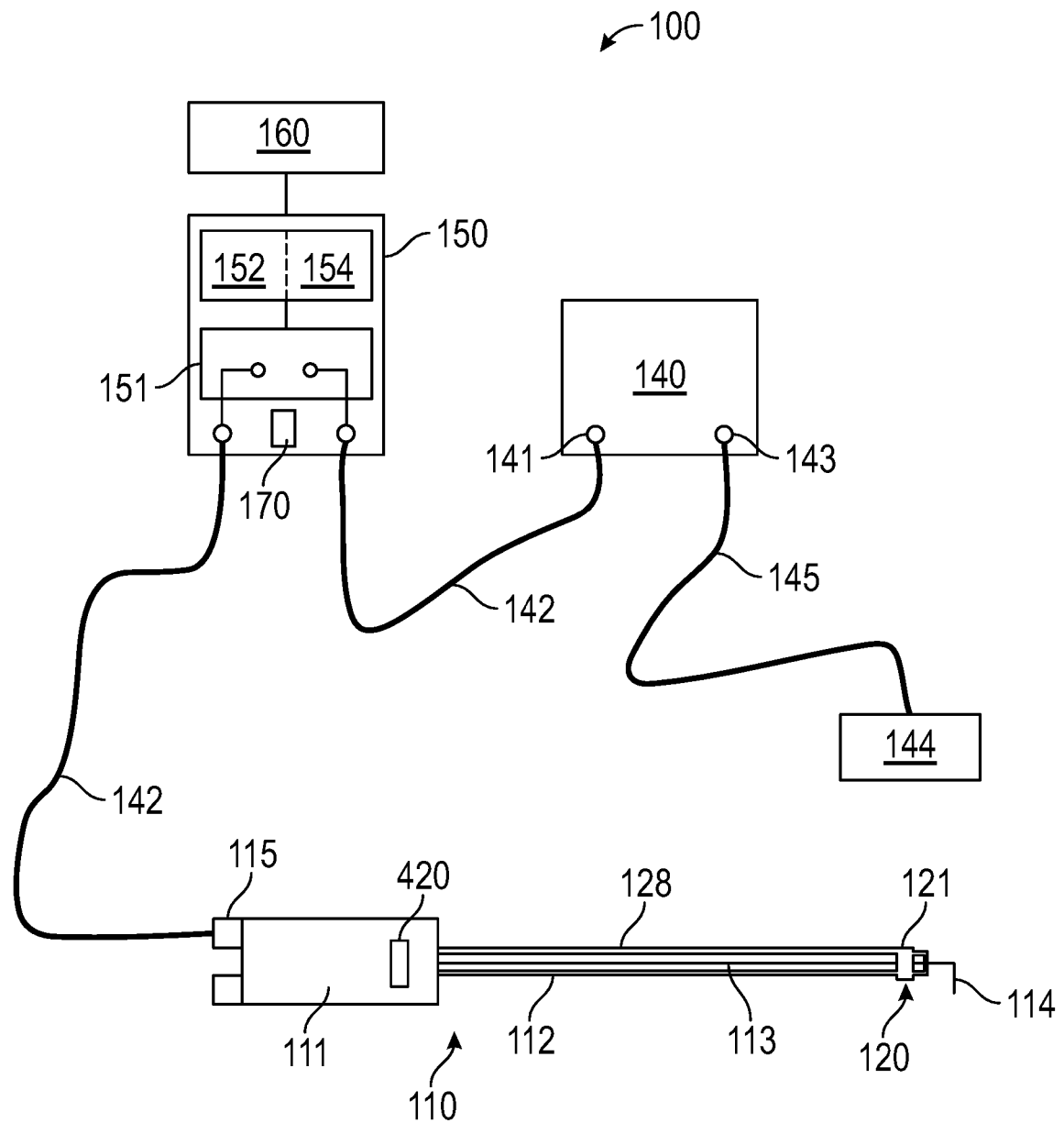
FIG. 1 is a schematic illustration of a surgical assembly according to an embodiment of the present invention.

Referring to FIG. 1 of the drawings, there is illustrated a surgical assembly 100 according to an embodiment of the present invention for use during a surgical procedure, such as an electrosurgical, ultrasonic or laser based surgical procedure. The assembly 100 comprises a surgical tool 110, which may typically comprise a tool which is held by the surgeon for cutting and/or cauterising tissue. In the embodiment illustrated, the tool 110 comprises a handle 111 and an elongate shaft 112 which is coupled at a proximal end thereof to the handle 111. The shaft 112 is formed of a dielectric material and comprises an electrical conductor 113, which extends through the shaft 112, typically along a longitudinal axis thereof. The conductor 113 extends out from a distal end of the shaft 112 and is thus electrically exposed, forming or joining to the tool-piece 114 that is responsible for delivering the energy to the tissue. The tool-piece is shaped to facilitate the surgical procedure and may comprise a wire formed into an arcuate section, or an L-section, or a jaws of a forceps or graspers, for example; or a jawed/grasper arrangement suitable for sealing of vessels, for example (not shown).

Figure 2:
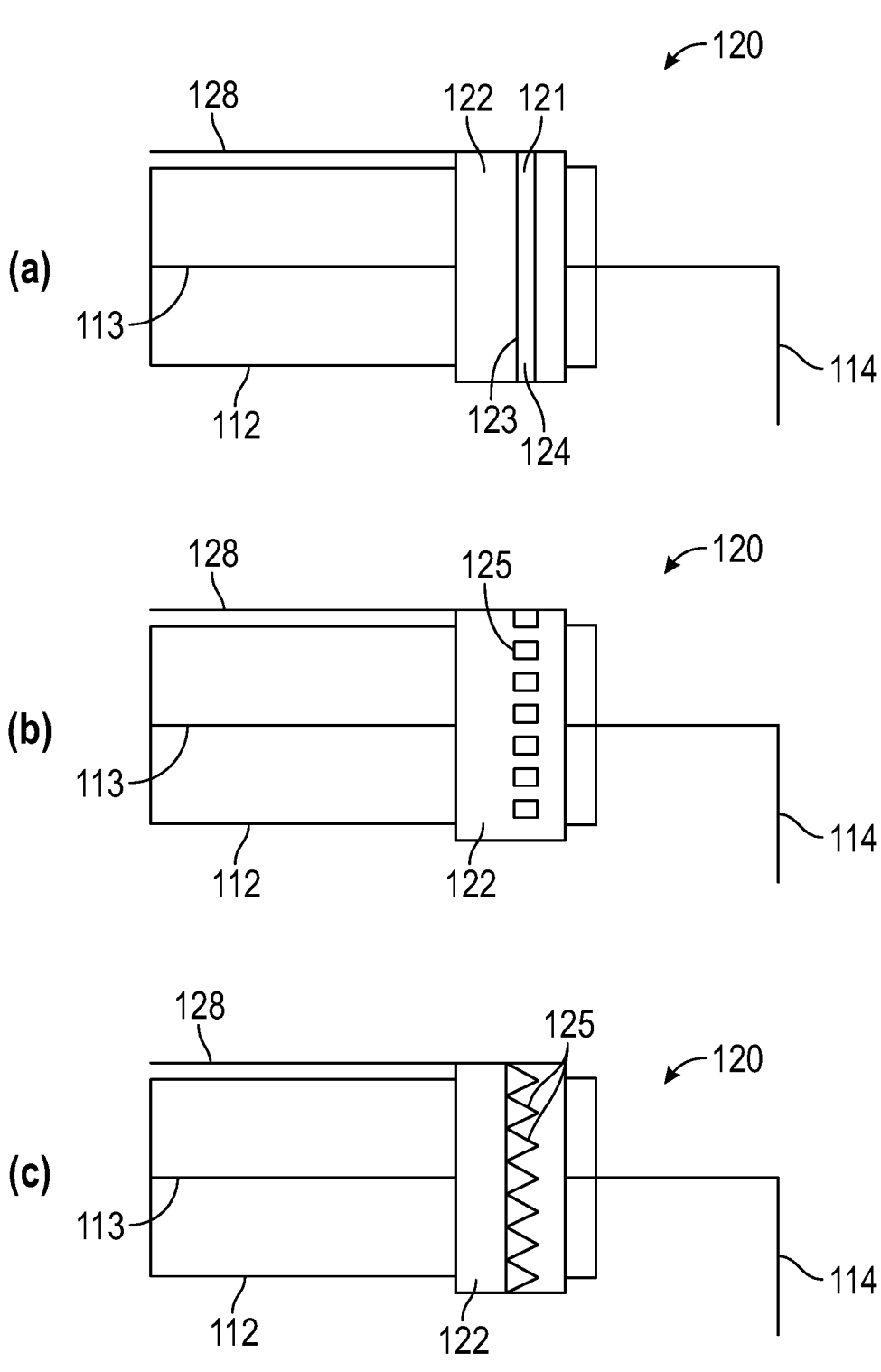
FIG. 2a-2i are schematic illustrations of embodiments of an electrode mounted upon a surgical tool.
FIG. 2j is a schematic illustration of a side view of an electrode mounted upon a forceps.
FIG. 2k is a plan view of the electrode and forceps illustrated in FIG. 2j.
Figure 2:
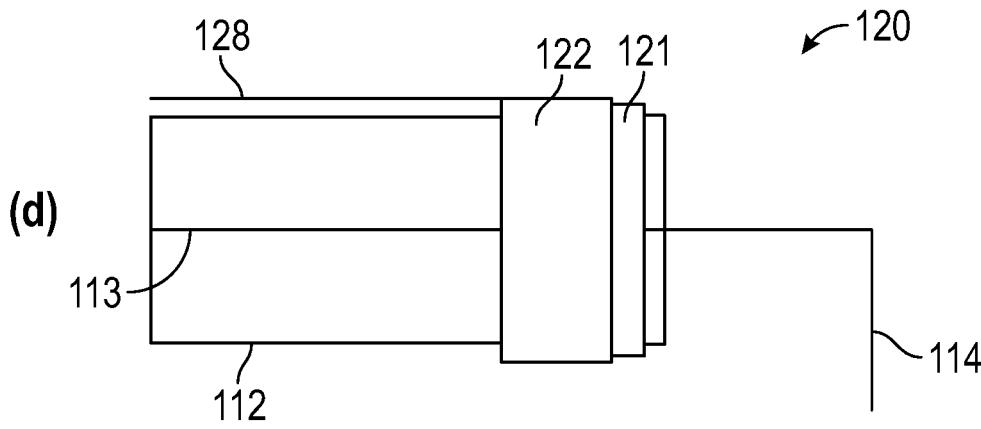
Figure 2:
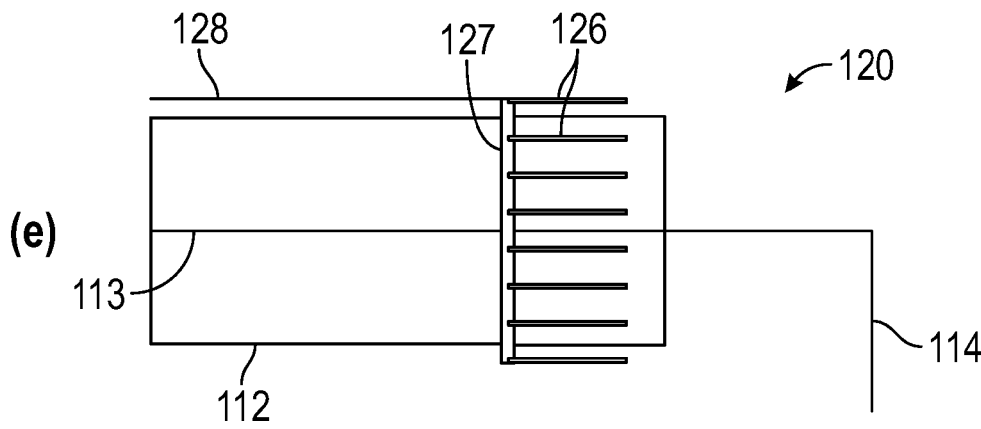
Figure 2:
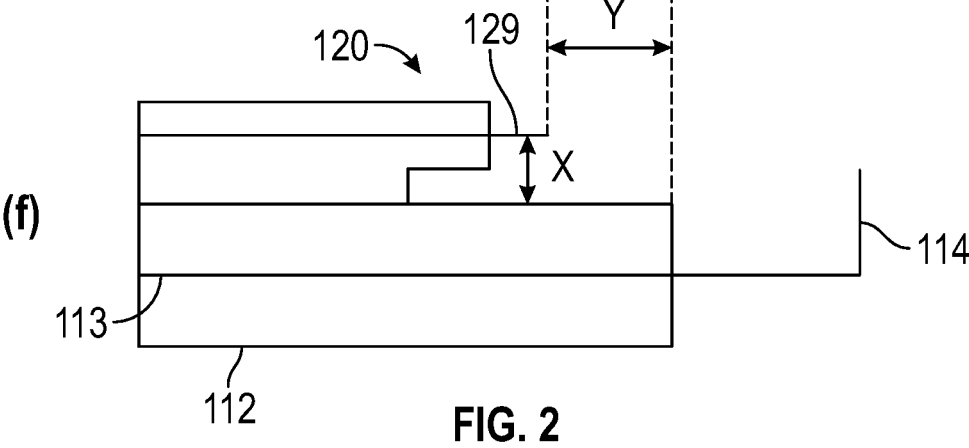
Figure 2:
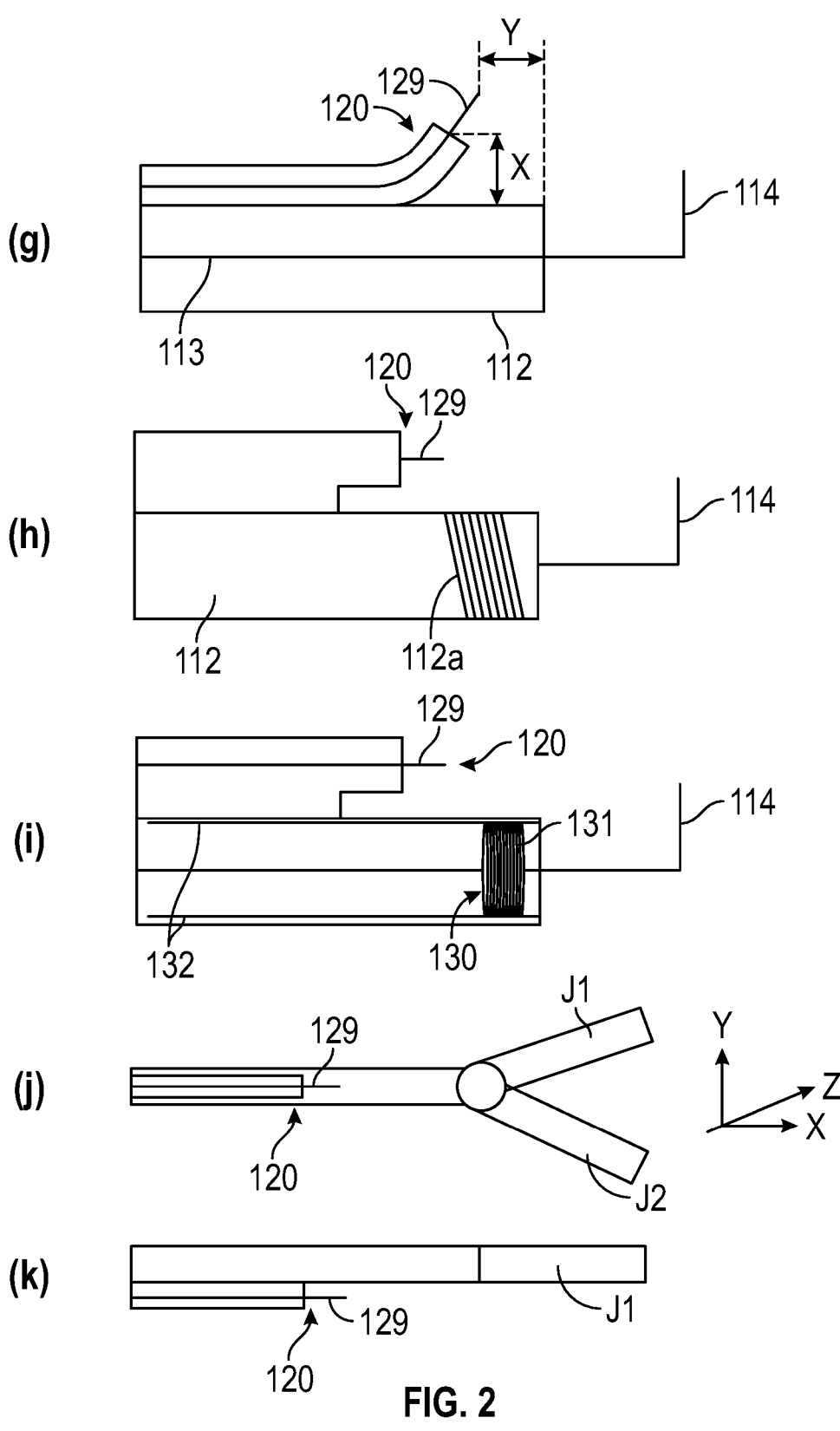

Referring to FIGS. 1 and 2 of the drawings, the assembly 100 further comprises an electrode 120 disposed upon the tool shaft 112, proximate a distal end thereof. In a first embodiment, the electrode 120 extends circumferentially around the shaft 112 and is centred upon a longitudinal axis of the shaft. The electrode 120 comprises an electrically conductive collar 121 which is encased within an electrically insulative sheath (not shown) or carrier 122. In this respect, the carrier 122 is disposed radially between the collar 121 and the shaft 112 of the tool 110 and thus acts to minimise any electrical current flowing directly between the collar 121 and the conductor 113 which extends along the tool 110. The electrode collar 121 is electrically exposed circumferentially thereof, along a radially outward facing side of the electrode 120, by a circumferentially extending window 123 formed in the radially outward facing side of the carrier 122, thus exposing a ring shaped portion 124 of the collar (FIG. 2a). In an alternative embodiment, the carrier 122 may comprise a plurality of windows 125 formed in the radially outward facing side of thereof, which are angularly separated around the electrode 120, for electrically exposing portions of the collar 121. The windows 125 may comprise a square (second embodiment—FIG. 2b) or triangular shape (third embodiment—FIG. 2c), or a combination thereof for example, and act to electrically expose shaped portions of the collar 121. In each of the first, second and third embodiments of the electrode, the collar 121 is arranged to project through the opening(s) in the carrier 122 and thus extend above an outer surface of the carrier 122. The raised portions of the collar 121 facilitates the emission of electrons therefrom for ionising particulate material. In a fourth embodiment as illustrated in FIG. 2d of the drawings, the collar 121 may extend longitudinally of the shaft 112, beyond a distal end of the carrier 122, to electrically expose a distal edge or ring of the collar 121 (FIG. 2d). In this case, the distal edge may be sharpened to similarly facilitate the emission of electrons. In a further alternative embodiment (which is not illustrated), the collar 121 may be patterned directly to form the desired shaping and disposed upon the radially outward facing side of the carrier 122, rather than being encased within the carrier 122 and the desired shaping of the exposed portions of the collar 121 being determined by the shaping of the windows in the carrier 122.

In a fifth embodiment (as illustrated in FIG. 2e of the drawings), the electrode 120 may instead comprise a plurality of electrically conductive elongate elements 126, such as electrically exposed wires, orientated in a substantially parallel orientation, and parallel with a longitudinal axis of the shaft 112 of the tool 110. The elements 126 are angularly separated around the shaft 112 and are electrically coupled at their proximal ends by an electrically conductive ring 127 which extends circumferentially around the tool shaft 112.

The electrode 120 of each of the above embodiments further comprise an electrically conductive pathway 128 which extends from the respective collar 121 of the first-fourth embodiments or ring 127 of the fifth embodiment, along the shaft 112 toward the handle 111, where the pathway terminates at an electrical connector 115. The pathway 128 may comprise an electrically insulated wire for example and, via the connector 115, is arranged to electrically communicate an electrical signal from an electrical generator 140 to the collar 121 or ring 127. The generator 140 may comprise a high voltage electrical generator capable of generating 1.5-20 kV, preferably 3-10 kV, and is arranged to generate a direct current (DC) voltage waveform that is used for establishing an electrical field from the electrically exposed portions of the collar 121 or elongate elements 126, proximate a site of a surgical procedure.

In a sixth embodiment, as illustrated in FIGS. 2f and 2g of the drawings, the electrode 120 comprises an elongate rod or wire 129 having a sharpened distal end. The electrode 120 may extend substantially parallel to the longitudinal axis of the shaft 112 (FIG. 2f) or diverge away from the shaft 112 in a direction which is along the shaft 112 toward a distal end thereof (FIG. 2g). In both situations, a proximal end of the electrode 120 is radially spaced from an outer surface of the shaft 112 by a first offset X and a distal end of the electrode 120 is longitudinally spaced from a distal end of the shaft 112 (namely where the conductor 113 becomes exposed), by a second offset Y. In situations where the tool-piece 114 comprises a forceps for example, as shown in FIG. 2j of the drawings, the first offset is directed out of a plane in which the jaws J1, J2 of the forceps rotate. In this respect, in situations where the jaws rotate in an x-y plane for example, then the first offset extends laterally out of the x-y plane, and comprises a component to the separation which is along the z-axis.

The first and second offsets X, Y minimise any undesirable electrical tracking/conductance directly between the electrode 120 and the conductor 113 or tool-piece 114, caused by a build-up of conductive material (not shown), such as fluid and tissue resulting from the surgical procedure, upon the shaft 112. The build-up of conductive material on the shaft 112 provides an electrical pathway between the exposed wire 129 of the electrode 120, and tool-piece 114, and this pathway can be further reduced by profiling an outer surface of the shaft 112 with an external thread 112a or corrugations as illustrated in FIG. 2h of the drawings. The profiling reduces the tendency of the conductive material to distribute (creep) along the shaft 112, by preferentially causing the material to follow the profiling 112 around the shaft 112 (thereby increasing the creepage distance).

The electrodes 120 described above in connection with each of the first to sixth embodiments may be enclosed within a sheath (not shown) and retractably deployable relative to the sheath to expose the electrode 120, by an actuator (not shown). Upon retracting the electrode 120 relative to the sheath, the sheath is arranged to wipe the electrode 120 and thus remove conductive material from the electrode 120. In situations where the sheath (not shown) is retractable relative to the shaft 112 then the sheath may also be further arranged to remove any conductive material from the shaft to further minimise any electrical tracking between the electrode 120 and the tool-piece 114.

As an alternative to the sheath, or in addition thereto, the assembly 100 may comprise a heater 130 disposed upon the tool shaft 112, longitudinally between the distal end of the shaft 112 and the electrode 120, as illustrated in FIG. 2i of the drawings. The heater 130 may comprise a coil 131 of encapsulated resistive wire for example which extends around the shaft 112, or which may be embedded within the shaft 112, and which is electrically coupled to an electrical supply (not shown) via transfer wires 132 for supplying electrical current through the resistive coil 131. The passage of electrical current through the coil 131 is arranged to heat the region of the shaft 112 disposed longitudinally between the electrode 120 and the tool-piece 114 for drying any conductive material and fluid disposed around the shaft 112, to minimise the development of an electrical pathway between the electrode 120 and the tool-piece 114.

Figure 3:
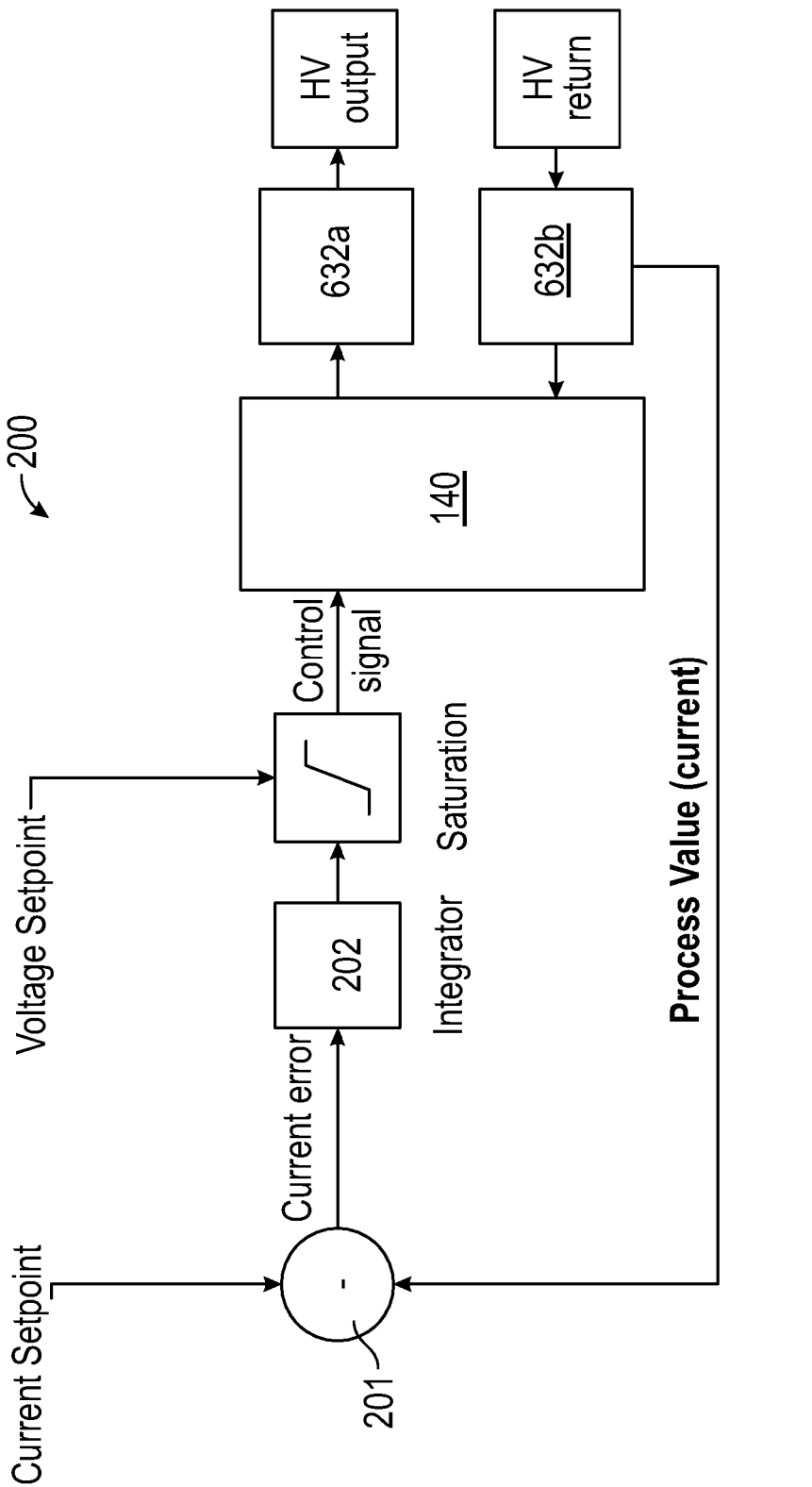
FIG. 3 is a schematic illustration of a circuit diagram illustrating the closed loop current control circuit.

Referring to FIG. 3 of the drawings, the electrical generator 140 comprises an analogue closed loop control circuit 200 for closed loop control of the output current from the electrode 120, through the patient. The operating current is influenced by the separation of the distal end of the electrode 120 from the patient tissue. As the electrode 120 approaches the patient tissue, the impedance falls. This causes the current to increase and the output voltage between the electrode 120 and patient to fall. The electrical generator 140 however, monitors the current flowing between the electrode 120 and the patient tissue and terminates the current as it approaches 10 µA, which is typically the maximum DC current that can safely be applied to a patient. As a result, the voltage falls below a level that is sufficient to cause electrostatic precipitation.

The control circuit 200 primarily controls the output current of the electrical generator 140. The electrical generator 140 comprises a 200 MΩ series resistance 632 (see FIG. 7) at the output thereof to ensure that a maximum current of 50 µA under a single short circuit fault condition, i.e. if the current limit fails and the electrical generator 140 outputs the maximum voltage. The resistance is embodied as two separate 100 MΩ resistors 632a, 632b (see FIG. 7) each separately connected in series with the high voltage and low voltage output terminals of the electrical generator 140. Electrical current is returned to the electrical generator 140 via a resistor (see FIG. 7), thereby developing a voltage that is buffered and used as a process value. This value is compared with a current set point using a comparator 201 and the resulting error is integrated via integrator 202 providing a control signal for the electrical generator 140. If the process value is above/below the current set point, the control signal to the electrical generator 140 reduces/increases. This reduces/increases the high voltage output and increases/reduces the measured current toward the target set point value.

It is possible for the error signal to become saturated as the electrical generator output saturates at approximately 10 kV, thereby limiting the current available. The closed loop circuit 200 is designed to saturate at a variable level, allowing the output saturation voltage to be adjusted below 10 kV whenever the process value current is below the set point.

This output resistance of the electrical generator 140 imposes an unwanted voltage drop at the output under normal operating conditions, creating a dependency between the voltage available at the output and the current being drawn. Practically, problems occur where the corona current is close to the typically 10 µA patient current limit. Voltage drop across the series resistance 632 reduces the output voltage below what is required for efficient corona, namely ionisation of smoke particulates. Smoke clearing performance is impaired by the mandated current limit, not because of insufficient current available, but because there is insufficient voltage.

Figure 4:
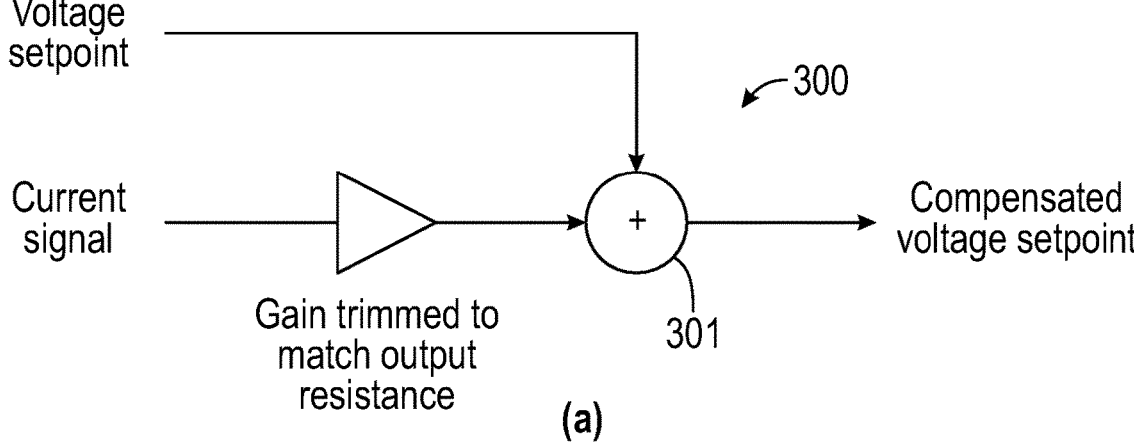
FIG. 4a is a schematic illustration of a voltage compensation circuit.
FIG. 4b is a graphical representation of the output voltage at the distal end of the tool-piece, as a function of electrical current.
Figure 4:
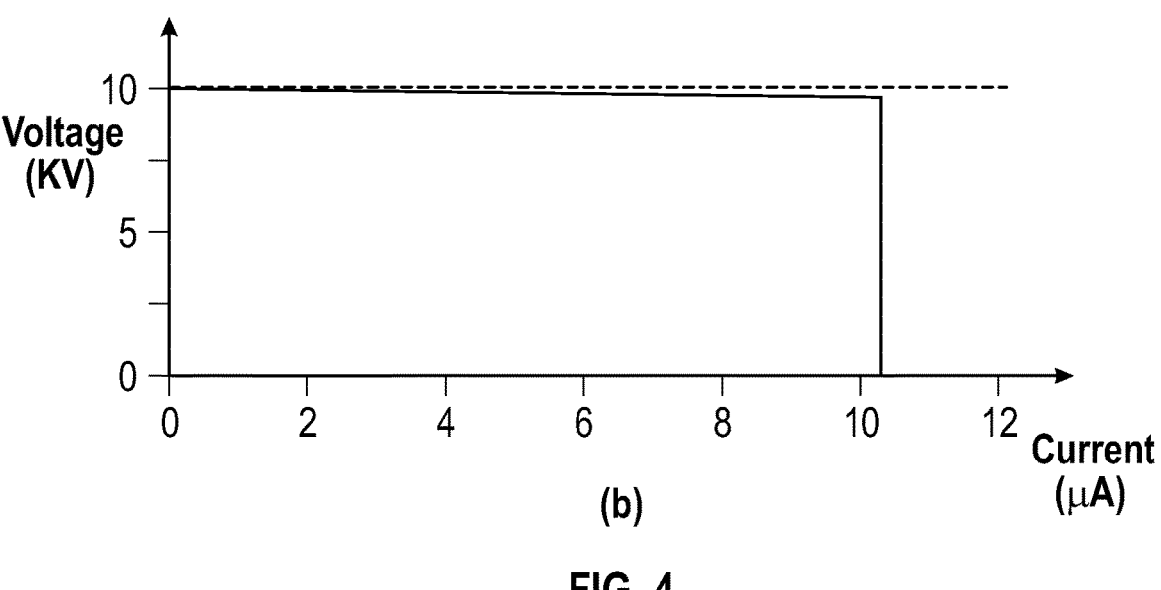

However, the voltage drop can be compensated using a voltage compensation circuit 300, as illustrated in FIG. 4*a*, which is configured to engineer a corresponding increase in the voltage output from the electrical generator 140. This is achieved by increasing the voltage set point by the voltage drop through the series resistance 632. The circuit comprises a processor 301 or summation device which is arranged to receive as input the desired or target voltage and a signal representative of an electrical current flowing through the resistance 632 This current is already known by the closed loop control circuit 200; the process value of the control circuit is representative of the current through the series resistance. Accordingly, by adding a proportion of the current signal to the set point achieves the desired voltage compensation. Operating with this circuit 300 results in a near flat load curve, as illustrated in FIG. 4*b* of the drawings, up to the current limit. This ensures that the ionisation efficiency no longer reduces with increasing current, provided that the electrical generator 140 has not reached the voltage saturation point.

Figure 5:
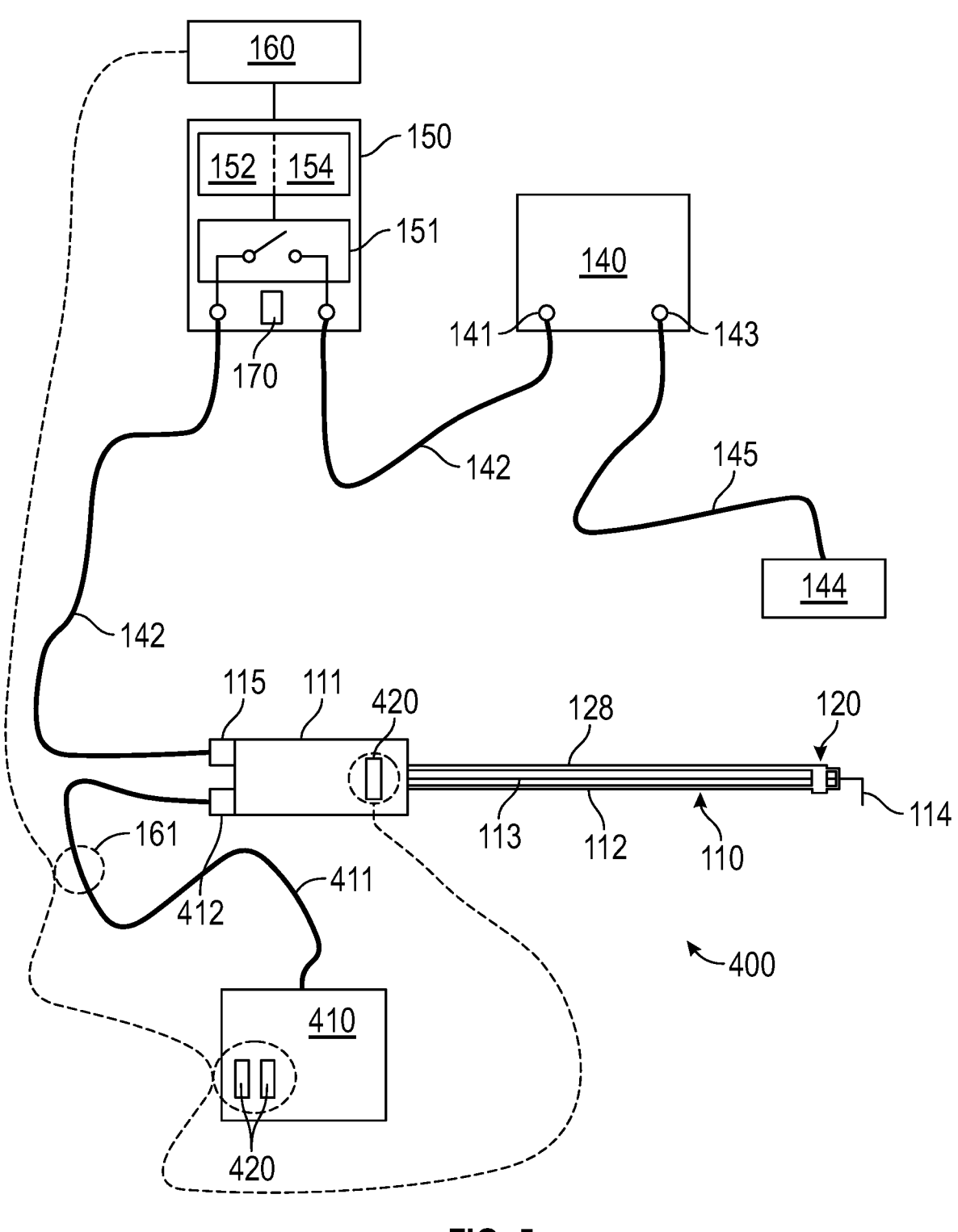
FIG. 5 is a schematic illustration of a surgical system according to an embodiment of the present invention.

Referring to FIG. 5 of the drawings, there is illustrated a surgical system 400 according to an embodiment of the present invention, for use in performing a surgical procedure on a patient. The system 400 comprises the surgical assembly 100 as described above (and shown in FIG. 1), and a surgical generator 410 for generating a surgical signal along the tool 110 to the tool-piece 114, for use in performing the surgical procedure. In an embodiment in which the tool-piece 114 comprises an electrical conductor, the surgical generator 410 may comprise an electrosurgical generator for generating an electrical current surgical signal along the wire 113 within the shaft 112. However, in an alternative embodiment, it is envisaged that the shaft 112 may comprise a waveguide (not shown) for communicating an ultrasonic or lasing surgical signal from a respective ultrasonic or laser surgical generator, for performing the required surgical procedure.

The assembly 100 and system 400 further comprise a controller 150 for controlling the application of the electrical current along the electrical pathway 128 of the electrode 120 from the electrical generator 140 to the collar/ring/wire 121/127/129. The controller 150 comprises a switching arrangement 151 for enabling and disabling the application of the electrical current to the electrode 120 in dependence of an activation status of the surgical signal. The activation status is determined by a sensing arrangement 160 of the assembly 100, which may be arranged to directly sense the operation of actuators 420 for actuating the surgical signal, or alternatively directly sense the surgical signal from the surgical generator 410, such as via a current sensor 161. The sensing arrangement 160 is arranged to output a sensing signal to the controller 150 in dependence of the activation status, so that the controller 150 can determine whether to enable/disable the electrical current to the electrode 120.

During use, the electrode 120 is electrically coupled with an electrical pole 141 of the electrical generator 140 with a cable 142, via the switching arrangement 151. The cable is terminated at a connector (not shown) for connecting with the connector 115 on the handle 111 of the tool 110. The patient is electrically coupled to the further electrical pole 143 of the electrical generator 140 via a contact pad 144 which is applied to the patient's leg (not shown) for example, and a further connecting cable 145. The tool 110 is then electrically coupled with the surgical generator 410 for performing the surgical procedure, via a further connecting cable 411 and connector 412 disposed on the handle 111. When the surgeon activates the surgical signal, which maybe via a button 420 on the tool handle 111, a pedal on a footswitch (not shown) for example, or a button 420 on the surgical generator 410 itself, the sensing arrangement 160 is arranged to output a sensing signal to the controller 150 to cause the controller 150 to simultaneously enable the electrical current to flow to the electrode 120 by closing the switching arrangement 151. The electrical supply to the electrode 120 thus establishes an electric field between the exposed portions of the collar 121, or conductive elements 126, or wire 129, and the patient, thereby attracting ionised particulates held in suspension proximate the surgical site toward the patient for example, to clear the surgeons view. It is evident therefore that the controller 150 enables the electrode 120 to facilitate particulate clearing at the time the surgical signal is commenced.

When the sensing arrangement 160 senses that the actuators 420 of the surgical generator 410 have been manipulated to remove the surgical signal, or when the sensing arrangement 160 senses that the surgical signal has been removed from the tool 110, namely disabled, then the sensing arrangement 160 is arranged to output a sensing signal to the controller 150 which causes the controller 150 to open the switching arrangement 151 thereby inhibiting further electrical current from flowing to the electrode 120 and thus removing the electrical field.

However, in an alternative embodiment, the controller 150 further comprises a timer 152 which enables the controller 150 to delay the disablement of the electrical signal to the electrode 120 for a predetermined time, such as 1-10 seconds, after the surgical signal has been removed. This enables the electrode 120 to maintain the electrical field to the patient even after the surgeon has finished with an aspect of the surgical procedure for example, so that smoke and particulate clearing can continue even after the aspect of the procedure has been completed.

Figure 6:
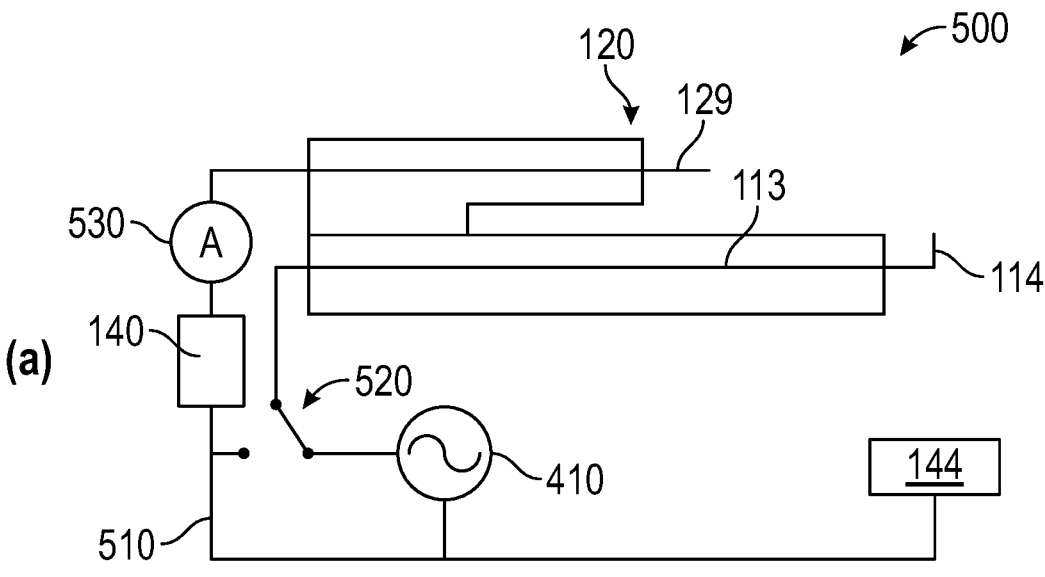
FIG. 6 is a schematic illustration of a monitoring circuit for monitoring the build-up of conductive material on the shaft of the surgical tool.
Figure 6:
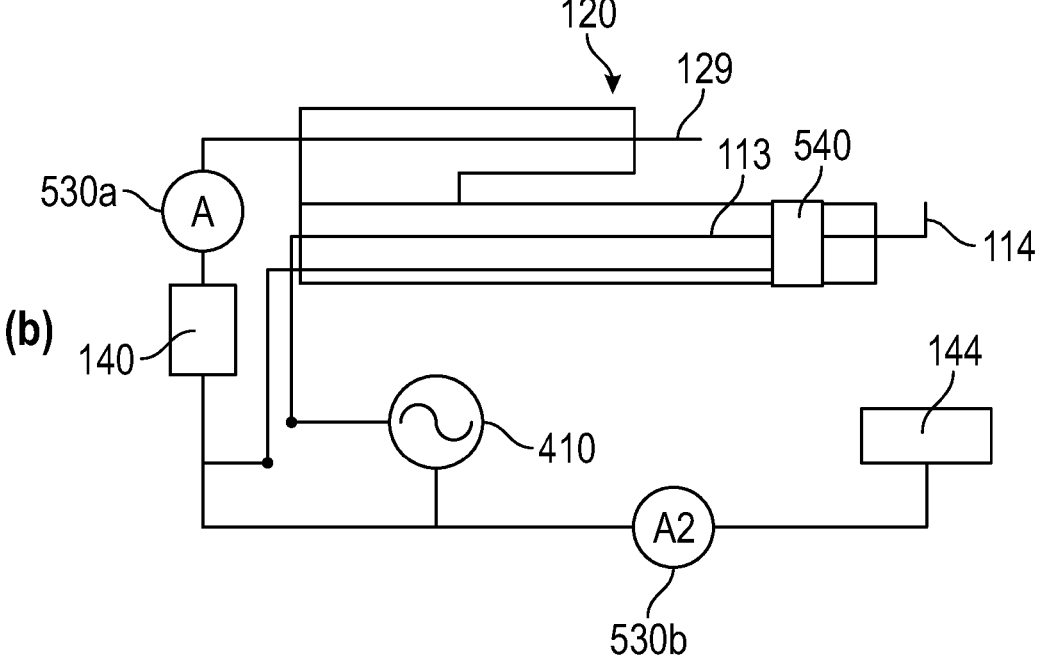

In an embodiment, the assembly 100 further comprises a monitoring circuit 500 for monitoring the build-up of conductive material on the shaft 111 of the tool, between the electrode 120 and tool-piece 114. A schematic illustration of the monitoring circuit 500 is illustrated in FIG. 6 of the drawings and includes a series electrical pathway 510 comprising the tool-piece 114, conductor 113, electrical generator 140 and electrode 120. The pathway 510 is interrupted by the separation of the tool-piece 114 from the electrode 120, and a switch 520 which, in the embodiment illustrated in FIG. 6*a*, remains open (namely switched to the surgical generator 410) during the application of the surgical signal to the tool-piece 114. However, following the removal of the surgical signal from the tool-piece 114, the switch 520 is arranged to close via an instruction from the controller 150, thereby establishing an electrical pathway between the tool-piece 114 and electrode 120 which is interrupted only by the physical separation of the tool-piece 114 from the electrode 120. Any conductive material disposed on the shaft 112, between the tool-piece 114 and electrode 120 will thus facilitate electrical current (generated from the electrical generator 130) to pass directly therebetween. The current flowing in the monitoring circuit 500 is thus indicative of the build-up of conductive material. For tools 110 completely devoid of conductive material on the shaft 112, then the physical separation of the tool-piece 114 and electrode 120 will prevent any electrical current flowing in the monitoring circuit 500. Conversely, in situations where the shaft 112 is heavily contaminated with conductive material, then electrical current will flow easily between the tool-piece 114 and electrode 120. Accordingly, by monitoring the electrical current flowing in the pathway 510 as by using an ammeter 530 disposed in series within the pathway 510, then the build-up of conductive material can be monitored and the shaft 112 cleaned (such as via the sheath (not shown) or heating coil 131 discussed above) before the voltage difference between the patient and the electrode 120 falls to unuseable levels. In situations where the shaft 112 is cleaned via the heating coil 131, then it is envisaged that the heating coil 131 may be disposed in a series configuration with the pathway 510 of the monitoring circuit 500 such that the heating generated will be dependent on the level of material disposed on the shaft 112.

The monitoring circuit 500 discussed above is enabled only following the removal of the surgical signal from the tool-piece 114. However, in an alternative embodiment, as illustrated in FIG. 6b of the drawings, the monitoring circuit 500 may comprise an electrically conductive guard collar or ring 540 disposed at the distal end of the shaft 112, on an exterior thereof, and the level of conductive material build-up on the shaft 112 is determined by monitoring the electrical current flowing between the electrode 120 and the ring 540, through the material via ammeter A1 530a, rather than between the electrode 120 and tool-piece 114 so that the build-up of material on the shaft 112 can be monitored. The monitoring circuit of this alternative embodiment further comprises a separate ammeter A2 530b so that the current flowing through the patient from the electrode 120 can be simultaneously monitored during the application of the surgical signal to the tool-piece 114, namely during use.

The monitoring circuit 500 illustrated in figured 6a and 6b is also arranged to monitor the total electrical current passing through the patient due to the electrical signal from the electrode 120. Upon referring to FIGS. 6a and 6b, during use of the tool-piece 114 and electrode 120, electrical current will pass through the patient, from electrode 120, and return to the respective generator 140 via the patient pad 144. The electrical current can thus be monitored during a surgical procedure and thus the current supply to the electrode 120 can be maximised to provide optimal ionisation, without exceeding the safe patient current limit The assembly 100 further comprises an override actuator 170 which may be disposed on the electrical generator 140, controller 150 (as illustrated in FIGS. 1 and 5 of the drawings), surgical tool 110 or a foot switch (not shown) for example, for enabling the surgeon to activate the electrical current to the electrode 120 for clearing particulate matter independently of the sensing signal. The override facility allows a surgeon to consciously position the tool 110 for smoke clearing for example, and further enable the surgeon to operate the switching arrangement 151 of the controller 150, for a bespoke period of time, to suitably clear particulate matter suspended near the surgical site.

Irrespective of whether the surgeon activates the surgical generator 410 (and thus initiates a call for the electrical signal to the electrode 120) or actuates the override actuator 170 to enable the electrical signal to the electrode 120, the application of the electrical (smoke clearing) signal to the electrode 120 is fundamentally controlled by the closed loop control circuit 200 which monitors the proximity of the electrode 120 to patient tissue. The control circuit 200 comprises a voltage monitoring device (not shown) for monitoring the voltage at the distal end of the electrode 120. In the event that the electrode 120 is sited too close to the abdominal wall (not shown), within the abdominal cavity of the patient for example, then the voltage will fall below a threshold value, owing to the reduced impedance between the electrode 120 and the patient tissue. This reduced voltage will be too low to create a suitable potential difference therebetween for ionising surgical particles and smoke. Moreover, in the event that the electrode 120 is too close to the patient tissue, then this could result in a direct electrical short through the patient upon applying the electrical signal. Accordingly, the control circuit 200 is configured to prevent/terminate the application of the electrical signal to the electrode 120 in the event that the collar/element/wire 121,126, 129 of the electrode 120 is positioned or becomes positioned too close to the patient tissue, irrespective of any demand or call for the electrical signal.

Figure 7:
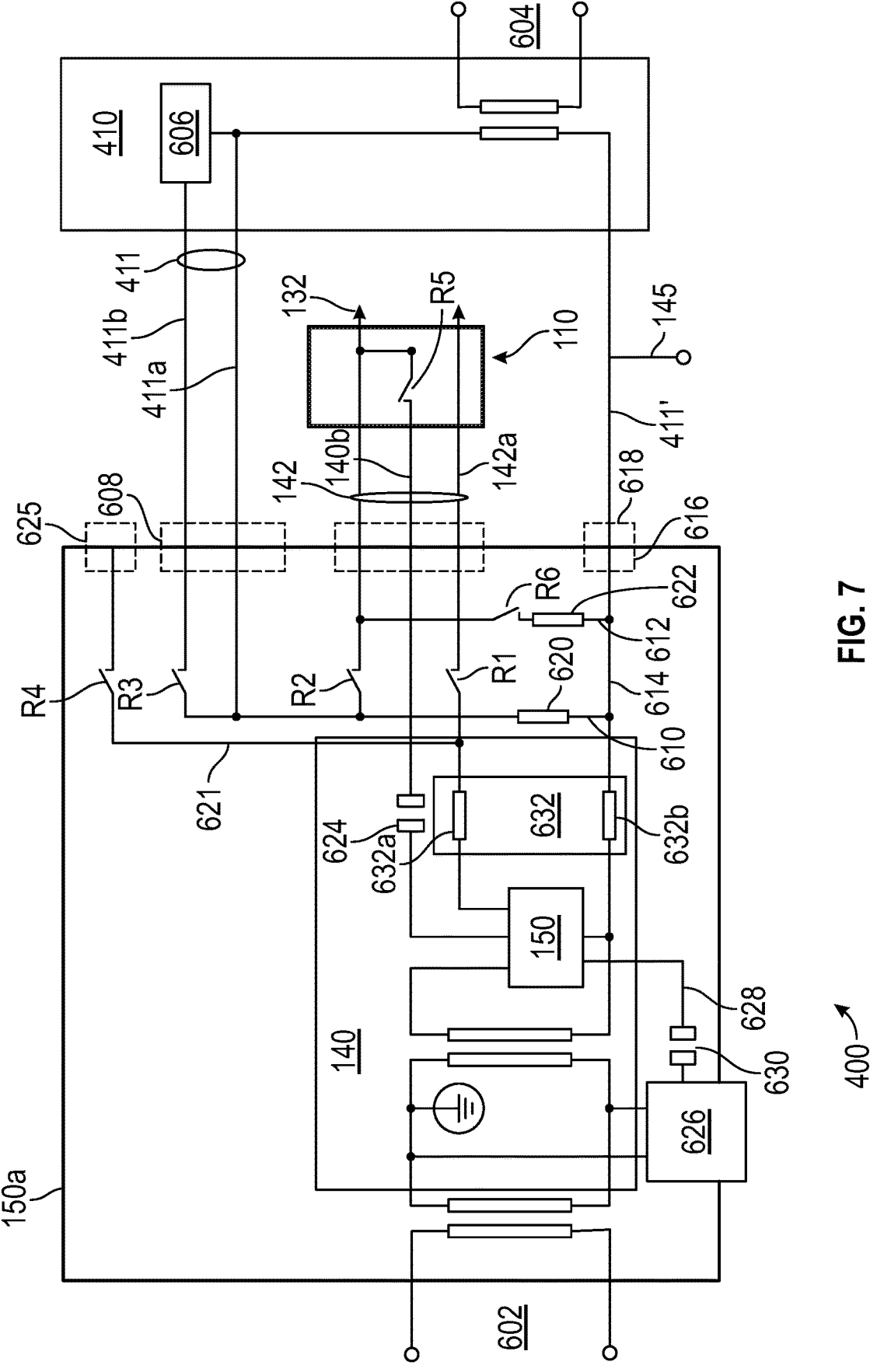
FIG. 7 is a schematic illustration of the circuit diagram of the surgical system illustrated in FIG. 5; and, FIG. 8 is a schematic illustration of an electrode assembly according to an embodiment of the present invention.

Referring to FIG. 7 of the drawings, there is provided a schematic illustration of a circuit diagram 600 of the surgical system 400 according to an embodiment of the present invention, but with the sensing arrangement 160 removed. The system 400 is arranged to receive ac mains electrical power via input terminals 602 and this ac mains is converted into dc using a rectification circuit (not shown) associated with the electrical generator 140. The high voltage output from the electrical generator 140 is provided to the hand-piece 110 via line 142a within cable 142. Line 142a comprises a relay R1, and the application of the electrical signal to the electrode 120 is dependent on the switched state of this relay R1.

The surgical generator 410 is similarly arranged to receive ac mains electrical power via input terminals 604 and generate a first, namely surgical signal which is output via an interface 606. The surgical signal is communicated to the hand-piece 110 and thus the tool-piece 114 via a cable 411 and connector 608. Cable 411 comprises a line 411a with a relay R2 disposed therein and a cable 411b with a relay R3 disposed therein. Cable 411 comprises a length which is minimized to reduce capacitance between the patient circuit and the environment, and also reduce capacitance between the poles of the surgical generator output. This tends to reduce RF leakage currents (and thus lower the risk of burns to the operator or patient) and reduce the risk of low frequency (mains) leakage current, which is an electrocution hazard, to the patient. On some systems, the RF displacement/capacitive currents which are increased by lengthening treatment cables are significant compared to surgical effect currents (surgical plasmas are often high impedances) and this results in an attenuation of the intended treatment waveform.

The system 400 circuit further comprises a first and second electrical pathway 610, 612 coupled either side of relay R2 and which extend to a return or ground pathway 614. The pathway 614 extends to a terminal 616 on the housing 150a of the controller 150. The second pole 143 or return of the electrical generator 140 is electrically coupled to this pathway 614 via cable 411'. The cable 411' comprises a connector 618 disposed at a distal end thereof for electrically coupling with terminal 616. The first pathway 610 is electrically coupled at the high voltage side of relay R2 and comprises a series connected bleed resistor 620 (having a resistance value in the range of 1 MΩ-300 MΩ, and preferably 50 MΩ-200 MΩ) disposed therein. The bleed resistor 620 acts to encourage the dissipation or discharge of residual charge arising from the application of the first signal. The resistance of the bleed resistor 620 is selected to suitably attenuate the residual portion of the surgical signal appearing across the output of the surgical generator 410 as the first signal is preferably limited to 10 μA. The bleed resistor 620 is a trivial addition to the loading presented to the second signal and as such, does not substantially affect the second signal. The second pathway 612 is electrically coupled at the low voltage side of the relay R2 and comprises a series connected relay R6 and a discharge resistor 622.

The circuit further comprises a relay R5 disposed in the tool handle 111 which is manually activated by the surgeon, such as via button 420. The relay R5 is disposed in an electrical pathway 142*b* which extends within cable 142 to the controller 150 for communicating the surgeon demands. The pathway 142*b* further comprises an electrical isolation element, such as a capacitor 624 for preventing DC current flowing to the controller 150.

The operational status of the tool-piece 114 and electrode 120 is provided as a visual output to the surgeon via the front panel indicator display 626. This display 626 is arranged to receive signals from the controller 150 via pathway 628 which also includes a protective capacitor 630 which prevents DC currents passing to the display 626.

Upon referring to FIG. 7, the circuit further comprises a separate electrical pathway 621 which is electrically coupled to line 142*a*, and which extends to a port 625 disposed on the housing 150*a*. Pathway 621 further comprises a series connected relay R4 which can be operated by the controller 150 to communicate the first signal to the port 625 in the event that a further electrode (not shown) is required to be electrically coupled to the electrical generator 140, for smoke clearing.

During an initialization process, relays R1 and R2 of the switching arrangement 151 are closed, with all other relays (R3-R6) of the switching arrangement 151 being open, so that any residual charge at the output of the surgical generator 410 is permitted to quickly discharge or dissipate across discharge resistor 620 for a period of 10 ms-100 ms. Following this initialization, relay R1 is opened. In this state, the system is in a standby condition with only R2 closed, ready for a demand from the surgeon.

When the surgeon demands the application of the surgical signal to the tool-piece 114 by actuating the button 181, relay R5 is closed, thereby instructing the controller 150 to close relay R3. While the button 181 is pressed, the surgical signal will be communicated to the tool-piece 114 and the sensing arrangement (not shown in FIG. 7) is configured to sense the activation of the surgical signal and close relay R1 to apply the electrical signal to the electrode 120 for smoke clearing. The application of the electrical signal to the electrode 120 causes electrons to emanate therefrom, and the electrons attach to the suspended particles thereby ionizing the particles. The electric field generated between the electrode 120 and the patient owing to the DC signal, subsequently causes the ionized particles to become attracted to the patient and thus away from the surgical site to improve the surgeons view thereof.

When the surgeon releases button 181, relay R5 is opened. The sensing arrangement 160 detects this release and communicates this button release to the controller 150, which results in relays R2 and R3 opening, thereby stopping the surgical signal from passing to the tool-piece 114. Following a time delay of approximately 5-10 seconds, relay R1 is subsequently opened by the controller 150 to remove the electrical signal from the electrode 120. However, if the surgeon requires extended smoke clearing for example, the then surgeon may press the override actuator 170 to cause the electrical signal to continue to pass to the electrode 120. Moreover, when the surgeon releases button 181 to remove the surgical signal from the tool-piece 114, then the controller 150 may cause relay R6 to close so that any residual capacitative charge developed at the tool-piece 114 can discharge through resistor 622.

However, the application of the electrical signal to the electrode 120 is contingent on the electrode 120 being positioned out of contact with the patient tissue, and sited a minimum distance from patient tissue, as determined by the closed loop control circuit 200. The control circuit 200 is configured to disable/prevent the application of the electrical signal to the electrode 120 regardless of any demand or call for the electrical signal, in the event that the electrode 120 is sited too close to patient tissue.

Figure 8:
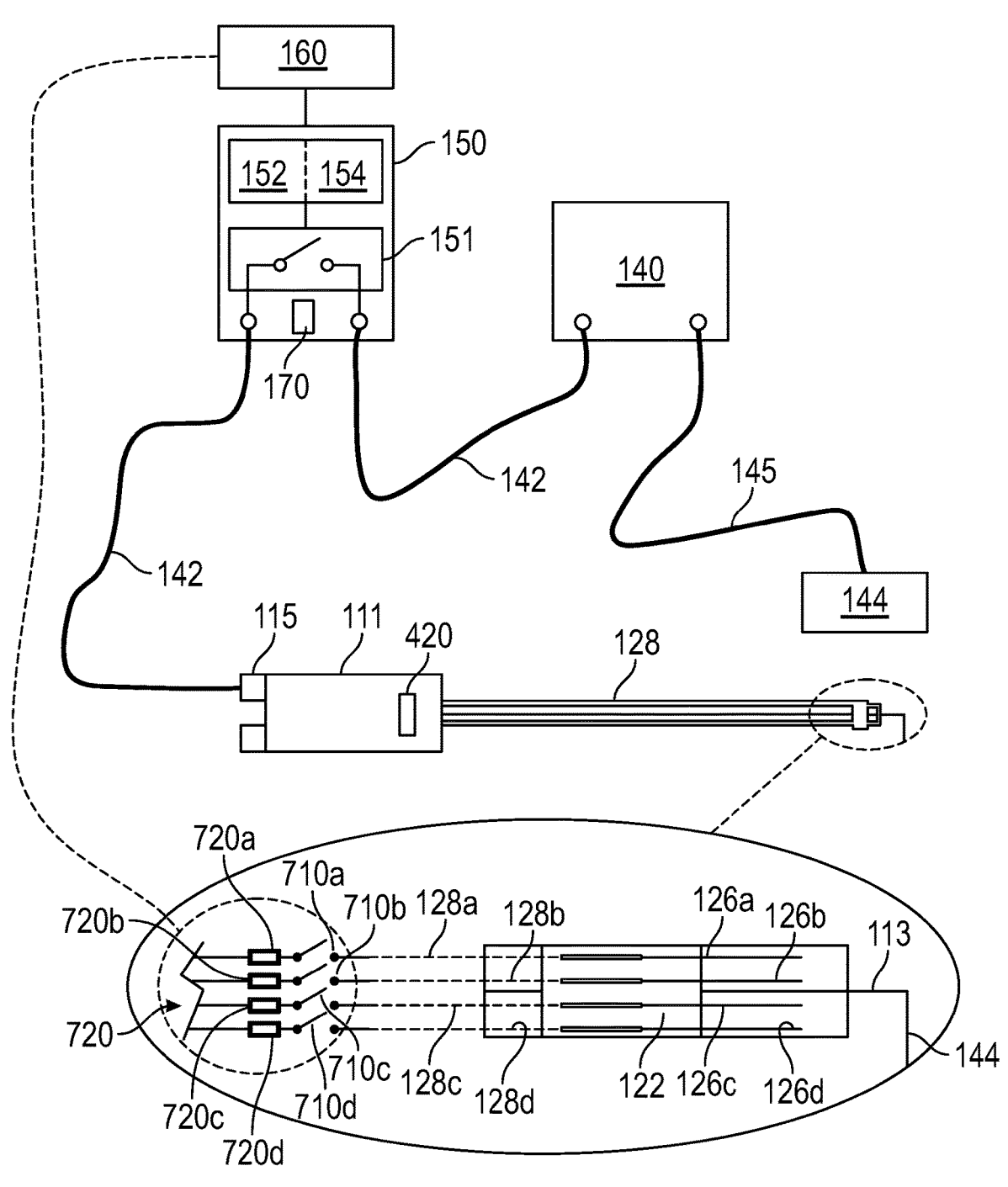

Referring to FIG. 8 of the drawings, there is illustrated an electrode assembly 700 according to an embodiment of the present invention for use with surgical tools 110 in reducing particulate matter, such as surgical smoke, generated during surgical procedures proximate a surgical site. The electrode assembly 700 may be used with the surgical assembly 100 and system 400 described above comprises an electrode comprising a plurality of electrically conductive elements 126*a-d*, each separately electrically couplable with an electrical generator 130 via a respective electrical pathway 128*a-d*, and configured to receive an electrical signal, namely an electrical current, from the generator 140.

The elements 126*a-d* are configured to a circular array via a carrier 122 which maintains an angular separation between the elements 126*a-d*, around the surgical tool 110. However, the skilled reader will recognize that the elements 126 may be configured to a differently shaped array, depending on the cross-sectional shape of the tool shaft 112. The elements 126 may comprise elongate electrical strips or wires for example which may be orientated in a substantially parallel configuration and parallel with a longitudinal axis of the tool 110. Each element 126 is arranged to receive an electrical current via a respective switch 710*a-d* disposed in the respective pathway 128*a-d*. The switches 710*a-d* form part of a switching arrangement 710 of the controller 150, and the controller 150 is arranged to operate each switch 710*a-d* of the arrangement 710 in dependence of a current sensing signal from an electrical current sensing arrangement 720.

The current sensing arrangement 720 comprises a plurality of electrical current sensors 720*a-d* each arranged to separately sense the electrical current flowing in a respective pathway 128*a-d*. In the event that a particular sensor 720*a-d* senses that the electrical current flowing in a particular pathway 128*a-d* exceeds a pre-defined threshold value, the sensing arrangement 720 outputs a signal to the controller 150 causing the controller 150 to open the switch 710*a-d* in the respective pathway 128*a-d* to electrically isolate the element 126*a-d*. In this respect, in situations where the one or more conductive elements 126*a-d* pass too close to the patient tissue, or otherwise contact the patient, the controller 150 is arranged to remove the electrical current flowing to the respective elements 126*a-d* to prevent any discharge of electrical current directly from the conductive elements 126*a-d* through the patient. This ability to effectively "switch-off" selected elements 126*a* and 126*b* (for example) enables the remainder of the elements 126*c* and 126*d* (for example) to continue to function as normal, and thus avoids the need for a complete shut-down of the electrode 120.

The controller 150 may further comprise a timing arrangement 154 for selectively opening and closing the switches 710*a-d* of the switching arrangement 710 in accordance with a timing sequence. It is envisaged that the timing arrangement 154 will permit the controller 150 to cyclically apply an electrical current to each conductive element 126*a-d* in turn for example, or otherwise apply electrical current to the conductive elements 126*a-d* in a particular order to generate a desired time varying electrical field from the elements 126*a-d*.

From the foregoing it is evident that the assembly and system enable a surgeon to cut patient tissue with a tool-piece and also remove particles generated from the cutting procedure with an electrode at the same time. The assembly and system thus provide for a more compact and functional surgical arrangement.

The invention claimed is:

1. A surgical assembly for use in performing a surgical procedure on a patient, the assembly comprising:

a surgical tool comprising a tool-piece disposed at a distal end thereof, the tool-piece being arranged to receive a first signal for use in cutting or cauterizing tissue of the patient during the surgical procedure;

an electrode disposed upon the tool, the electrode being offset from the surgical tool, such that a proximal end of the electrode is radially spaced from the surgical tool and a distal end of the electrode is longitudinally spaced from the distal end of the surgical tool;

a DC electrical generator communicatively couplable with the electrode, for generating a second signal for use in generating an electrical field from the electrode proximate a site of the surgical procedure, for removing particles suspended proximate the surgical site by electrostatic precipitation;

a controller for controlling the application of the second signal to the electrode;

a sensing arrangement communicatively coupled with the controller, the sensing arrangement being arranged to sense an activation status of the first signal and to output a sensing signal to the controller in dependence of the activation status; and a bleed circuit comprising a bleed resistor configured to discharge from the tool piece a residual charge generated by the second signal, wherein:

the controller is arranged to enable the application of the second signal to the electrode only upon receiving a sensing signal representative of an activation of the first signal and the bleed resistor is configured to discharge the residual charge throughout the activation of the second signal.

2. A surgical assembly according to claim 1, wherein the controller is arranged to disable the application of the second signal to the electrode upon receiving a sensing signal representative of a deactivation of the first signal.

3. A surgical assembly according to claim 1, wherein the controller comprises a timer for disabling the application of the second signal to the electrode a predefined time after receiving a sensing signal representative of a deactivation of the first signal.

4. A surgical assembly according to claim 1, further comprising an override actuator for enabling the application of the second signal to the electrode independently of the activation status of the first signal.

5. A surgical assembly according to claim 1, further comprising a heater for heating a region of the surgical tool disposed longitudinally between the electrode and the distal end of the surgical tool.

6. A surgical assembly according to claim 1, wherein the tool comprises a handle and a shaft which is coupled at a proximal end thereof to the handle, and wherein the electrode is disposed proximate a distal end of the shaft and wherein the shaft comprises a profiled outer surface at least in the region disposed longitudinally between the electrode and the distal end of the shaft.

7. A surgical assembly according to claim 1, further comprising an electrically conductive pathway which extends from the electrode to a proximal end of the tool, for communicating the second signal from the electrical generator to the electrode.

8. A surgical assembly according to claim 1, wherein the bleed resistor is configured to discharge the residual charge from the tool-piece to the patient.

9. A surgical assembly according to claim 1, wherein the bleed resistor is configured to discharge the residual charge from the tool-piece throughout the activation of the first signal.

10. A surgical assembly according to claim 1, wherein the resistance of the bleed resistor is 50 MΩ-200 MΩ.

11. A surgical assembly for use in performing a surgical procedure on a patient, the assembly comprising:

a surgical tool comprising a tool-piece disposed at a distal end thereof, the tool-piece being arranged to receive a first signal for use in cutting or cauterizing tissue of the patient during the surgical procedure;

an electrode disposed upon the tool, the electrode being offset from the surgical tool, such that a proximal end of the electrode is radially spaced from the surgical tool and a distal end of the electrode is longitudinally spaced from the distal end of the surgical tool;

a DC electrical generator communicatively couplable with the electrode, for generating a second signal for use in generating an electrical field from the electrode proximate a site of the surgical procedure, for removing particles suspended proximate the surgical site by electrostatic precipitation;

a controller for controlling the application of the second signal to the electrode; and a sensing arrangement communicatively coupled with the controller, the sensing arrangement being arranged to sense an activation status of the first signal and to output a sensing signal to the controller in dependence of the activation status; and a bleed circuit comprising a bleed resistor configured to discharge from the tool-piece a residual charge generated by the second signal;

the controller is arranged to enable the application of the second signal to the electrode only upon receiving a sensing signal representative of an activation of the first signal the bleed resistor is configured to discharge the residual charge throughout the activation of the second signal; the electrical generator comprises a closed loop control circuit for monitoring a proximity of the electrode to patient tissue; and the closed loop control circuit comprises a voltage monitoring device for monitoring the voltage at a distal end of the electrode such that, in the event that the voltage at the distal end of the electrode falls below a threshold value indicative of the electrode being positioned too close to the patient tissue to create a potential difference between the electrode and the patient tissue for ionizing surgical particles and smoke, the closed loop control circuit prevents/terminates the application of the second signal to the electrode.

12. A surgical assembly according to claim 11 further comprising a current monitoring device for monitoring the current at a distal end of the electrode such that, in the event that the current at the distal end of the electrode exceeds a threshold value indicative of the electrode being positioned too close to the patient tissue to create a potential difference between the electrode and the patient tissue for ionizing surgical particles and smoke, the closed loop control circuit prevents/terminates the application of the second signal to the electrode.

13. A surgical system for use in performing a surgical procedure on a patient, the system comprising:

a surgical tool comprising a tool-piece disposed at a distal end thereof, a surgical generator communicatively couplable with the tool-piece, for generating a first signal for use in cutting or cauterizing tissue of the patient during the surgical procedure;

an electrode disposed upon the tool, the electrode being offset from the surgical tool, such that a proximal end of the electrode is radially spaced from the surgical tool and a distal end of the electrode is longitudinally spaced from the distal end of the surgical tool;

a DC electrical generator communicatively couplable with the electrode, for generating a second signal for use in generating an electrical field from the electrode proximate a site of the surgical procedure, for removing particles suspended proximate the surgical site by electrostatic precipitation;

a controller for controlling the application of the second signal to the electrode; and a sensing arrangement communicatively coupled with the controller, the sensing arrangement being arranged to sense an activation status of the first signal and to output a sensing signal to the controller in dependence of the activation status; and a bleed circuit comprising a bleed resistor configured to discharge from the tool piece a residual charge generated by the second signal, wherein:

the controller is arranged to enable the application of the second signal to the electrode only upon receiving a sensing signal representative of an activation of the first signal and the bleed resistor is configured to discharge the residual charge from the tool-piece throughout the activation of the second signal.

\* \* \* \* \*